United States Patent [19]

Burri et al.

[11] 4,317,775

[45] Mar. 2, 1982

[54] AMOXICILLIN DERIVATIVES

[75] Inventors: Kasper F. Burri, Kaiseraugst, Switzerland; Perry Rosen, North Caldwell, N.J.

[73] Assignee: Hoffmann-La Roche Inc., Nutley, N.J.

[21] Appl. No.: 110,275

[22] Filed: Jan. 7, 1980

[51] Int. Cl.$^3$ ............................................. C07D 499/70
[52] U.S. Cl. ............................... 260/239.1; 260/347.5; 260/347.8; 424/271
[58] Field of Search ....................... 260/239.1; 424/271

[56] References Cited

U.S. PATENT DOCUMENTS

| | | | |
|---|---|---|---|
| 3,198,788 | 8/1965 | Granatek | 260/239.1 |
| 3,198,804 | 8/1965 | Johnson et al. | 260/239.1 |
| 3,230,214 | 1/1966 | Fosker et al. | 260/239.1 |
| 3,248,387 | 4/1966 | Alburn et al. | 260/239.1 |
| 3,325,479 | 6/1967 | Fosker et al. | 260/239.1 |
| 3,647,781 | 3/1972 | Wieslogle et al. | 260/239.1 |
| 3,888,848 | 6/1975 | Higuchi et al. | 260/239.1 |

*Primary Examiner*—Natalie Trousof
*Assistant Examiner*—Vera C. Clarke
*Attorney, Agent, or Firm*—Jon S. Saxe; George M. Gould; William H. Epstein

[57] ABSTRACT

The compound 6-[D(-)alpha-amino-phenylacetamido]-penicillanic acid and salts or hydrates thereof wherein the amino group is substituted with a 5 to 6-membered heterocyclic ring, useful as antibacterial therapeutic agents in the treatment of infectious diseases caused by Gram-positive and Gram-negative bacteria and which are stable in aqueous solutions.

5 Claims, No Drawings

AMOXICILLIN DERIVATIVES

BACKGROUND OF THE INVENTION

6-[D(-)-alpha-amino-phenylacetamido]-penicillanic acids have the formula:

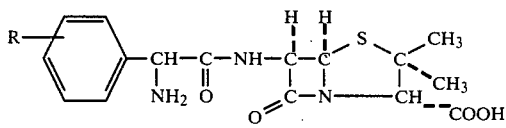

wherein R is hydrogen or hydroxy have a broad spectrum of activity against both gram-positive and gram-negative bacteria. Oral administration results in high blood levels. Among the compounds of formula I are amoxicillin and ampicillin.

However, the only dosage forms available for the compounds of formula I are for parenteral or intravenous administration by means of water-soluble salts. These salts in aqueous solutions have a very short half-life.

Various aldehyde and ketone condensation products of alpha-aminopenicillins of formula I are known. For example, derivatives of various alpha-aminopenicillins with nitro-substituted heterocyclic aldehydes are disclosed in U.S. Pat. No. 3,647,781. Other patents and patent publications disclosing derivatives of alpha-aminopenicillins with aldehydes and ketones include U.S. Pat. Nos. 3,198,804 and 3,558,602 (various aldehydes and ketones), U.S. Pat. No. 3,198,788 (formaldehyde), U.S. Pat. No. 3,230,214 (aromatic or heteroaromatic aldehydes containing an ortho hydroxyl substituent), U.S. Pat. No. 3,325,479 (diketones), U.S. Pat. Nos. 3,489,746, 3,549,746, 3,814,800 and U.K. Pat. No. 1,224,619 (acetone), U.S. Pat. No. 3,725,389 (N-substituted-4-piperidones), U.S. Pat. No. 3,888,848 (chloral hydrate), DOS 2,258,994 (various aldehydes including acetaldehyde) and South African Pat. No. 72/8474 (acetaldehyde).

These condensation products of the alpha-aminopenicillins of formula I with aldehydes or ketones result in the formation of either an imidazolidinyl compound or a Schiff base or mixtures thereof. These condensation products are readily soluble in water and more stable than the corresponding salts. They are, in fact, bioprecursors of the corresponding alpha-aminopenicillin since they are readily converted in vivo to the corresponding alpha-aminopenicillins. However, the in vivo liberation of the ketone or aldehyde can cause adverse and/or toxic side effects.

It is, therefore, an object of this invention to prepare new water-soluble forms of alpha-aminopenicillins for oral and parenteral administration, which are stable in aqueous systems and do not have the deleterious side effects as seen for ketone and aldehyde adducts.

SUMMARY OF INVENTION

This invention relates to penicillin derivatives having enhanced stability in aqueous solution and useful as antibacterial therapeutic agents. These derivatives have the following formula:

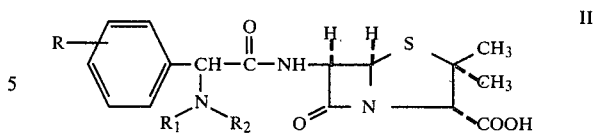

wherein R is hydrogen or hydroxy; $R_1$ and $R_2$ are individually hydrogen, or a saturated heterocyclic 5 to 6 membered ring containing one hetero atom selected from the group consisting of oxygen or sulfur, said hetero atom being positioned in said ring adjacent the carbon atom in said ring connected to the nitrogen atom, said ring being unsubstituted or substituted in one or more positions with lower alkyl or halogen; with the proviso that at least one of $R_1$ and $R_2$ is other than hydrogen as well as salts, hydrates, or esters thereof.

DETAILED DESCRIPTION

The term "lower alkyl" as used herein designates saturated aliphatic hydrocarbon radicals containing from 1 to 7 carbon atoms such as methyl, ethyl, propyl, isopropyl, butyl, etc. The term "halogen" includes all four halogens such as chlorine, fluorine, iodine and bromine, with chlorine and fluorine being especially preferred.

The novel and useful compounds of this invention include the compound of formula II, its salts, hydrates and esters thereof. Any conventional pharmaceutically acceptable salt or ester are included within the compound of formula II.

The compounds of the present invention include the pharmaceutically acceptable non-toxic esters of the compound of formula II. Suitable esters include those which hydrolyze readily in the body to produce the parent acid, for example, lower alkoxy-lower alkyl esters such as methoxymethyl esters, acyloxy-lower alkyl or benzyl esters such as acetoxymethyl, pivaloyloxymethyl, alpha-acetoxyethyl, alpha-acetoxybenzyl and alpha-pivaloyloxyethyl esters; lower alkoxycarbonyloxy-lower alkyl esters, such as ethoxycarbonyloxymethyl and alpha-ethoxycarbonyloxyethyl; and lactone, thiolactone and dithiolactone esters. Also lower alkanoyloxy esters are suitable.

Suitable salts of the compound of formula II include metal salts, e.g. alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxyethyl)-amine, tris(-hydroxymethyl)amine or tris-(2-hydroxyethyl)amine, cycloalkylamines such as bicyclohexylamine, or with procaine, dibenzylamine, N,N-dibenzylethylenediamine, l-ephenamine, N-ethylpiperidine, N-benzyl-beta-phenethylamine, dehydroabietylamine, N-N'-bis-dehydroabietylethylenediamine, or bases of the pyridine type such as pyridine, collidine or quinoline, or other amines which have been used to form salts with benzylpenicillin.

Where either or both $R_1$ or $R_2$ are a heterocyclic ring, these heterocyclic rings have the formula:

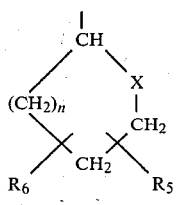

where n is an integer from 1 to 2; and X is selected from sulfur or oxygen; $R_5$ is hydrogen, halo or lower alkyl, and $R_6$ is hydrogen, halo or lower alkyl.

Among the heteroaromatic rings that are preferred are included tetrahydrofuran-2-yl, 2H-tetrahydropyran-2-yl, tetrahydrothiophen-2-yl, 2H-tetrahydro-thiopyran-2-yl. Among the heteroaromatic rings that are particularly preferred are the foregoing group which are unsubstituted, substituted only with a halo substituent, substituted only with a lower alkyl substituent and substituted with both a halo and lower alkyl substituent.

The claimed compounds of this invention are prepared by reacting an alkali metal salt of a compound of the formula:

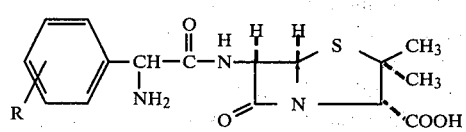

where R is as above with a compound of the formula:

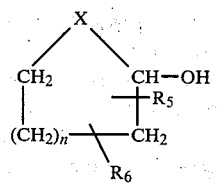

wherein n, X, $R_5$ and $R_6$, are as above.

The compound of formula IV is reacted with a compound of formula V to form the compound of formula II. In carrying out this reaction, it is generally preferred to utilize an aqueous medium. In general, this reaction is carried out in the presence of an inorganic alkali metal base such as sodium hydroxide, potassium hydroxide, lithium hydroxide, etc. In carrying out the reaction, temperature and pressure are not critical. This reaction can be carried out at room temperature and atmospheric pressure. If desired, higher or lower temperatures can be utilized.

After reaction between the compound of formulas IV and V is carried out, the compound of formula II can be recovered from the reaction medium in its acid form by neutralizing the reaction medium before isolating the compound of formula II from the reaction medium. If hydrolyzable esters of the compound of formula II are desired, the compound of formula II can be esterified by any conventional means.

The compounds of formula V are generally known compounds. In general, the lower alkyl and halo substituted ring compounds of formula V where the halo group is a substituent on the carbon atoms of the ring alpha to the hydroxy group, i.e. a compound of the formula:

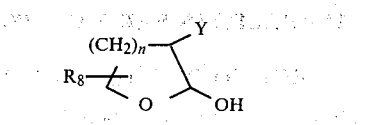

where $R_8$ is lower alkyl and Y is halogen and n is as above can be prepared from compounds of the formula:

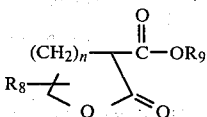

where $R_8$ is as above; and $R_9$ is lower alkyl and n is as above via the following intermediates:

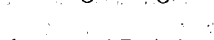

wherein $R_8$, $R_9$, Y and n are as above.

The compound of formula X is converted to the compound of formula XI by treating the compound of formula X with a halogenating agent. Any conventional halogenating agent can be utilized for carrying out this reaction. Among the preferred halogenating agents are included perchloryl fluoride, which is a fluorinating agent. Any of the conditions conventional in utilizing these halogenating agents can be utilized in carrying out the conversion of the compound of formula X to the compound of formula XI. The compound of formula XI is converted to the compound of formula XII by hydrolysis followed by decarboxylation. Decarboxylation can be carried out utilizing conventional methods disclosed in the art. In general, decarboxylation is carried out by heating the compound of formula XI in its acid form at temperatures of from 120° to 160° C. for a period of from 5 to 10 hours.

The compound of formula XII is converted to the compound of formula V-A by treating the compound of formula XII with a reducing agent. Among the reducing agents which can be utilized to carry out this reaction are di-isobutyl aluminum hydrides and disiamyl borane. Any of the conditions conventional in utilizing these reducing agents can be utilized in carrying out this reaction.

The compounds of this invention exhibit antibacterial activity similar to amoxicillin and ampicillin both in vitro and in vivo. These compounds of formula I, their salts, hydrates and esters are active against microorganisms such as S. pyogenes, E. coli and K. pneumoniae.

The compounds of this invention can be administered orally, parenterally or topically in suitable dosage forms and may also be administered in the form of their salts or esters. The compounds of this invention are stable in solution and are, thus, particularly advantageous for use when parenteral administration is indicated.

The compounds of this invention can be combined with conventional compatible organic or inorganic pharmaceutical carrier materials including, for example, water, gelatin, gums, lactose, starches, magnesium stereate, talc, vegetable oils, polyalkylene glycols, petroleum jelly and the like. These pharmaceutical preparations can be in unit dosage form or solution. These preparations can also contain other therapeutically active substances or conventional pharmaceutical adjuvants such as preservatives, stabilizing agents, wetting agents, emulsifying agents, buffers and the like.

The pharmaceutical preparations can be in conventional solid dosage forms such as tablets, capsules, dragees and the like, semi-solid forms such as ointments and creams, conventional dosage forms such as suppositories, dry ampules and the like.

Dosage forms for parenteral use are prepared by dissolving a powder of a salt of the active compound with suitable sterile aqueous solvent prior to use. Since the compounds of this invention are relatively stable, a solution can be formed many hours prior to use rather than immediately prior to use.

Typical suitable solvents include water for injection USP. Typical suitable intravenous solutions include sodium chloride injection (saline) USP, dextrose injection, e.g., 5% or 10% USP and the like. The injection solutions can contain preservatives.

The amount of active compound to utilize in treating bacterial infections varies with the needs of the patient in the judgment of the clinician. Generally, however, a sufficient amount of a compound of this invention is administered to parallel the dosage regimen of amoxicillin or ampicillin, i.e., the normal adult usually is administered from about 250 mg. to about 500 mg. about 3 or 4 times a day.

For injection from about 200 mg to about 500 mg equivalent of amoxicillin or ampicillin in 1 to 2 ml are injected 3 to 4 times a day.

Oral dosage forms contain from about 250 mg to about 500 mg equivalent of amoxicillin or ampicillin in, e.g., capsules. For parenteral use, concentrations of from about 100 mg/ml to about 250 mg/ml are acceptable.

Compound II, {2S-[2α, 5α, 6β(S*)]}-6-[bis(tetrahydro-2H-pyran-2-yl)amino]{[(4-hydroxyphenyl)acetyl]amino}-3,3-dimethyl-7-oxo-4-thia-1-azabicyclo[3.2.0-]heptane-3-carboxylic acid, sodium salt, was selected to illustrate the relative stability in aqueous solutions of the compounds of this invention, at room temperature and at 5° C. The stability of the compound was determined in 0.9% saline solution, 5% aqueous dextrose solution and in water, both at room temperature and/or 5° C.

The results are reported in Table 1 below. Initial concentrations of Compound II in solution were calculated on the basis of amoxicillin.

| Solvent | Concentration mg/ml | Storage Conditions | Percent Retention |
| --- | --- | --- | --- |
| 0.9% saline | 2.30 | RT, 6 hrs | 96 |
| | | RT, 24 hrs | 91 |
| | | RT, 48 hrs | 84 |
| | 2.25 | RT, 6 hrs | 96 |
| | | RT, 6 hrs + 5° C., 192 hrs | 98 |
| | 2.20 | 5° C., 24 hrs | 100 |
| | | 5° C., 48 hrs | 100 |
| | 34. | RT, 6 hrs | 97 |
| | | RT, 24 hrs | 85 |
| | | RT, 48 hrs | 76 |
| | 29.1 | RT, 6 hrs | 97 |
| | | RT, 6 hrs + 5° C., 192 hrs | 100 |
| | 31. | 5° C., 24 hrs | 100 |
| | | 5° C., 48 hrs | 100 |
| 5% Dextrose in Water | 2.10 | RT, 6 hrs | 95 |
| | | RT, 24 hrs | 89 |
| | | RT, 48 hrs | 71 |
| | 2.10 | RT, 6 hrs | 95 |
| | | RT, 6 hrs + 5° C., 192 hrs | 73 |
| | 2.20 | 5° C., 24 hrs | 95 |
| | | 5° C. 48 hrs | 91 |
| | 30 | RT, 6 hrs | 96 |
| | | RT, 24 hrs | 92 |
| | | RT, 48 hrs | 83 |
| | 31 | RT, 6 hrs | 100 |
| | | RT, 6 hrs + 5° C., 192 hrs | 81 |
| | 33 | 5° C., 24 hrs | 94 |
| | | 5° C., 48 hrs | 84 |
| Aqueous Concentrate | 155 | 5° C., 24 hrs | 100 |
| | | 5° C., 48 hrs | 100 |

In 0.9% saline solution both the 0.2% and 3% solutions maintained 90% of their potency after storage for at least 8 days (192 hours) at 5° C. At room temperature, the 0.2% solution maintained 90% of its potency for about 24 hours while the 3% solution maintained 90% of its potency for less than 24 hours.

In 5% dextrose in water solution, the 0.2% solution maintained 90% of its potency at 5° C. for 48 hours while the 3% solution maintained 90% of its potency at 5° C. for less than 48 hours. At room temperature, both solutions maintained 90% of their potency for about 24 hours.

The following Examples illustrate this invention. In the Examples Dibal-H is di-isobutyl aluminum hydride. The ether used was di-ethylether.

EXAMPLE 1

5-Ethyl-tetrahydro-2-oxo-furancarboxylic acid ethyl ester

To a solution of sodium methoxide prepared from 27.6 g (1.2 mmole) of sodium in 600 ml. of absolute ethanol was added dropwise 192 g (1.2 mol) of diethylmalonate. At the end of the addition an additional 200 ml of ethanol was added to the thick suspension and the mixture stirred an additional 30 min. To the mixture was then added dropwise 86.4 g (1.2 mol) of 1,2-epoxybutane while cooling with an ice bath to prevent the temperature from rising above 40° C. The initial salt slowly went into solution followed by the precipitation of a second salt during the addition. An additional 200 ml of ethanol was added to facilitate good stirring. After stirring overnight 68 ml. of glacial acetic acid was added (pH~6) and the precipitate filtered and washed thoroughly with ether. The solvent was then removed under reduced pressure and the residue dissolved in 2 l of ether. The ether solution was washed, dried (MgSo4) and the ether removed under reduced pressure. Distillation of the residue afforded 166.5 g (75%) of 5-ethyl-tetrahydro-2-oxo-furancarboxylic acid ethyl ester: bp 112° C. (0.2 mm Hg).

EXAMPLE 2

5-Ethyl-3-fluorotetrahydro-2-oxo-furancarboxylic acid ethyl ester

To a suspension 21.4 g of sodium hydride in 1 liter of dry toluene was added dropwise 166 g (0.89 mol) of 5-ethyl-tetrahydro-2-oxo-furancarboxylic acid ethyl ester while argon was slowly passed thru the mixture. After the addition the mixture was stirred at 25° C. for 18 hr. To the resulting thick suspension was then added perchloryl fluoride with argon as a following gas. The internal temperature was maintained at 0°–5° C. by a dry ice-acetone bath which was cooled to −20°–30° C. When the internal temperature began to approach the bath temperature the perchloryl fluoride was added for an additional 15 min. followed by a rapid stream of argon at room temperature. The mixture was then filtered thru celite, the celite washed with ether and the solvent removed under reduced pressure. Distillation of the residue afforded 162.5 g (89%) of 5-ethyl-3-fluorotetrahydro-2-oxo-furancarboxylic acid ethyl ester: bp 103°–108° C. (0.3 mm Hg.).

Anal. Calcd for $C_9H_{13}FO_4$: C, 52.94; H, 6.42; F, 9.30. Found: C, 53.00; H, 6.36; F, 9.39.

EXAMPLE 3

5-Ethyl-3-fluorodihydro-2(3H)-furanone

To a solution of 178 g (3.17 mol) of potassium hydroxide in 712 ml of water was added 162 g (0.79 mol) of 5-ethyl-3-fluorotetrahydro-2-oxo-furancarboxylic acid ethyl ester. The mixture was stirred at 25° C. for 18 hr. The water was then removed under high vacuum at 50°–55° C. and the residue acidified with 1 N sulfuric acid to pH∼2. The mixture was then thoroughly extracted with ethyl acetate, the ethyl acetate solution dried (MgSO$_4$) and the solvent removed under reduced pressure to give 154 g of crude malonic acid derivative. Decarboxylation was effected by heating the neat malonic acid derivative in an oil bath at 150°–155° C. for 5 hr. The residue was then distilled to give 79 g (75%) of 5-ethyl-3-fluorodihydro-2(3H)-furanone: bp: 72°–74° (0.3 mm Hg).

Anal. Calcd for $C_6H_9FO_2$: C, 54.54; H, 6.87; F, 14.38. Found: C, 54.71; H, 6.93; F, 14.41.

EXAMPLE 4

5-Ethyl-3-fluorotetrahydro-2-furanol

To a solution of 19.8 g (0.15 mol) of 5-ethyl-3-fluorodihydro-2(3H)-furanone dissolved in 500 ml of dry tetrahydrofuran was added at −70° C., 128 ml of a 1.4 M toluene solution of Dibal-H. The solution was stirred at −70° C. for one hour and then added cautiously to ice water. The resulting mixture was adjusted to pH∼1 with 200 ml of 1 N hydrochloric acid and then extracted with methylene chloride. The solution was dried (MgSO$_4$) and the solvent removed under reduced pressure to give 20 g of crude product. Distillation afforded 13.13 g of 5-ethyl-3-fluorotetrahydro-2-furanol: bp 45°–46° C. (0.1 mm Hg).

Anal. Calcd for $C_6H_{11}FO_2$: C, 53.72; H, 8.27; F, 14.16. Found: C, 53.70; H, 8.33; F, 14.45.

EXAMPLE 5

{2S-[2α,5α, 6β(S*)]}-6-{[2-tetrahydrofuranylamino(4-hydroxyphenyl)acetyl]amino}-3,3-dimethyl-7-oxo-4-thia-1-azabicyclo[3.2.0]heptane-2-carboxylic acid sodium salt To a stirred suspension of 6.28 g (0.015 mol) of amoxicillin trihydrate in 150 ml of distilled water was added in one portion 15 ml of 1 N aqueous sodium hydroxide solution. The amoxicillin quickly dissolved and after two minutes 2.25 g (0.025 mol) of tetrahydro-2-furanol was added. After stirring at 25° C. for two minutes the solution was quickly frozen by means of a dry ice-acetone bath and then lyophilized for 22 hr. The resulting product {2S-[2α, 5α, 6β(S*)]}-6-{[2-tetrahydrofuranylamino(4-hydroxyphenyl)acetyl]amino}-3,3-dimethyl-7-oxo-4-thia-1-azabicyclo[3.2.0]heptane-2-carboxylic acid sodium salt (6.55 g) was obtained as a white powder.

Anal. Calcd for $C_{20}H_{24}N_3NaO_6S$: C, 52.51; H, 5.29; N, 9.19; S, 7.01; Na, 5.03. Found: C, 52.82; H, 5.90; N, 8.25; S, 6.09; Na, 4.38.

EXAMPLE 6

{2S-[2α, 5α, 6β(S*)]}-6-[Bis(tetrahydro-2H-pyran-2-yl)amino]{[(4-hydroxyphenyl)acetyl]amino}-3,3-dimethyl-7-oxo-4-thia-1-azabicyclo[3.2.0]heptane-3-carboxylic acid sodium salt To a stirred suspension of 6.28 g (0.015 mol) of amoxicillin trihydrate in 125 ml of distilled water was added in one portion 15 ml of a 1 N aqueous solution of sodium hydroxide. The amoxicillin was quickly dissolved and after two minutes 4.59 mg (0.045 mol) of tetrahydro-2H-pyran-2-ol was added. After stirring at 25° for two minutes the solution was quickly frozen and lyophilized for 72 hr. to give 8.43 g of {2S-[2α, 5α, 6β(S*)]}-6-[bis(tetrahydro-2H-pyran-2-yl)amino]{[(4-hydroxyphenyl)acetyl amino}-3,3-dimethyl-7-oxo-4-thia-1-azabicyclo[3.2.0]heptane-3-carboxylic acid sodium salt as a white powder.

Anal. Calcd for $C_{26}H_{34}N_3NaO_7S\cdot1.3\ H_2O$: C, 53.93; H, 6.37: N, 7.26; S, 5.54. Found: C, 53.20; H, 6.37; N, 6.97; S, 5.14.

EXAMPLE 7

{2S-[2α, 5α, 6β(S*)]}-6-{[tetrahydro-2-thienylamino-(4-hydroxyphenyl)acetyl]amino}-3,3-dimethyl-7-oxo-4-thia-1-azabicyclo[3.2.0)heptane-2-carboxylic acid sodium salt To a stirred suspension of 6.7 g (0.016 mol) of amoxicillin trihydrate in 125 ml of distilled water was added in one portion 16 ml of 1 N aqueous sodium hydroxide solution. The amoxillin quickly dissolved and after two minutes 4.99 g (0.048 mol) of tetrahydrothiophene-2-ol dissolved in 10 ml of absolute ethanol was added. After stirring for two minutes at 25° C. the solution was quickly frozen and lyophilized for 19 hr to give 8.36 g of {2S-[2α, 5α, 6β(S*)]}-6-{[tetrahydro-2-thienylamino-(4-hydroxyphenyl)acetyl]amino}-3,3-dimethyl-7-oxo-4-thia-1-azabicyclo[3.2.0]heptane-2-carboxylic acid sodium salt as a slightly yellow pungent smelling powder.

Anal. Calcd for $C_{20}H_{24}N_3NaO_5S_2\cdot2H_2O$: C, 47.14; H, 5,54; N, 8.25; S, 13.20. Found: C, 47.73; H, 5.75; N, 7.70; S, 12.58.

EXAMPLE 8

{2S-[2α,5α,6β(S*)]}-6-{Bis[ethyl-3-fluoro-2-tetrahydrofuranylamino-(4-hydroxyphenyl)acetyl]amino}-3,3-dimethyl-7-oxo-4-thia-1-azabicyclo-[3.2.0]heptane-2-carboxylic acid sodium salt To a stirred suspension of 5.028 g (0.012 mol) of amoxicillin trihydrate in 150 ml of distilled water was added in one portion 12 ml of a 1 N aqueous sodium hydroxide solution. The amoxicillin was quickly dissolved and after two minutes 4.83 g (0.036 mol) of 5-ethyl-3-fluorotetrahydro-2-furanol dissolved in 6 ml of absolute ethanol was added. After stirring for two minutes at 25° C. the solution was quickly frozen and lyophilized for 19 hr to give 7.44 g of {2S-[2α,5α,6β(S*)]}-6-{bis[ethyl-3 fluoro-2-tetrahydrofuranylamino-(4-hydroxyphenyl)-acetyl]amino}-3,3-dimethyl-7-oxo-4-thia-1-azabicyclo-[3.2.0]heptane-2-carboxylic acid sodium salt as a white powder.

Anal. Calcd for $C_{28}H_{36}F_2N_3NaO_7S \cdot 2H_2O$: C, 51.29; H, 6.14; N, 6.41; S, 4.89; F, 5.79. Found: C, 50.70; H, 6.25; N, 6.20; S, 5.17; F, 5:39.

EXAMPLE 9

The compounds of this invention, as well as amoxicillin itself, were tested to determine acute toxicity in mice when administered orally, subcutaneously and intraperitoneally.

In this Example, and the Examples that follow:

Compound I is {2S-[2α,5α,6β(S*)]}-6-{[2-tetrahydrofuranylamino(4-hydroxyphenyl)acetyl]amino}-3,3-dimethyl-7-oxo-4-thia-1-azabicyclo[3.2.0]heptane-2-carboxylic acid sodium salt;

Compound II is {2S-[2α,5α,6β(S*)]}-6-[bis(tetrahydro-2-H-pyran-2-yl)amino]{[(4-hydroxyphenyl)acetyl]amino}-3,3-dimethyl-7-oxo-4-thia-1-azabicyclo[3.2.0]heptane3-carboxylic acid sodium salt;

Compound III is {2S-[2α,5α,6β(S*)]}-6-{[tetrahydro-2-thienylamino-(4-hydroxyphenyl)acetyl]amino}-3,3-dimethyl-7-oxo-4-thia-1-azabicyclo[3.2.0]heptane-2-carboxylic acid sodium salt; and Compound IV is {2S-[2α,5α,6β(S*)]}-6-{bis[5-ethyl-3-fluoro-2-tetrahydrofuranylamino-(4-hydrophenyl)-acetyl]amino}-3,3-dimethyl-7-oxo-4-thia-1-azabicyclo-[3.2.0]heptane-2-carboxylic acid sodium salt.

Toxicity results are reported in Table 2 below.

TABLE 2

| | Acute Toxicity in Mice | | |
| | $LD_{50}$ = (mg/kg) | | |
| Compound | p.o. | s.c. | i.p. |
|---|---|---|---|
| I | 9100 | 4550 | 3217 |
| Amoxicillin | >10,000 | >10,000 | 3142 |
| II | >6311 | 4462 | 6311 |
| Amoxicillin | >10,000 | 7070 | 3535 |
| III | 558 | 598 | 668 |
| Amoxicillin | >10,000 | 7070 | 3150 |
| IV | 3959 | 2800 | 3519 |
| Amoxicillin | >10,000 | 5864 | 3150 |

In the foregoing table the following are the definition of the symbols used.
> = more than
p.o. = per os
s.c. = subcutaneously
i.p. = intraperitoneally.

EXAMPLE 10

The compounds of this invention, as well as amoxicillin, were tested to determine their in vitro activity against representative systemic Gram positive and Gram negative bacteria. MIC is the Minimum Inhibitory Concentration. MBC is the Minimum Bactericidal Concentration.

Results reported in Table 3(a) are reported as MIC defined above and results reported in Table 3(b) are reported as MBC defined above.

TABLE 3(a)

| | In vitro Activity | | | | | | | |
| | (a) Minimum Inhibitory Concentration (MIC) in μg/ml | | | | | | | |
| Organism | Amoxicillin | I | Amoxicillin | II | Amoxicillin | III | Amoxicillin | IV |
|---|---|---|---|---|---|---|---|---|
| Streptococcus pyogenes | .098 | .022 | 0.31 | 0.39 | 0.195 | 0.554 | 0.024 | 0.027 |
| Streptococcus pneumoniae I | .012 | .022 | 0.039 | 0.049 | — | — | — | — |
| Staphylococcus aureus | .195 | .177 | 0.078 | 0.098 | 0.195 | 0.138 | 0.098 | 0.055 |
| Escherichia coli | 6.25 | 5.69 | 3.125 | 3.94 | 3.125 | 4.44 | 3.125 | 3.5 |
| Klebsiella pneumoniae | .39 | .71 | 0.39 | 0.09 | 0.39 | 0.554 | 0.195 | 0.218 |
| Salmonella schottmuelleri | .78 | .71 | 0.78 | 0.98 | — | — | — | — |
| Salmonella typhosa | .39 | .35 | 0.31 | 0.12 | — | — | — | — |
| Proteus vulgari | — | — | — | — | 1.56 | 0.554 | — | —. |
| Streptococcus pneumonia II | — | — | — | — | — | — | 0.024 | 0.013 |

TABLE 3(b)

| | In vitro Activity | | | | | | | |
| | (a) Minimum Inhibitory Concentration (MBC) in μg/ml | | | | | | | |
| Organism | Amoxicillin | I | Amoxicillin | II | Amoxicillin | III | Amoxicillin | IV |
|---|---|---|---|---|---|---|---|---|
| Streptococcus pyogenes | 3.125 | 2.84 | 5.0 | 6.31 | >6.25 | >8.88 | >0.39 | >0.218 |
| Streptococcus pneumoniae I | .024 | .022 | 0.039 | 0.049 | — | — | — | — |
| Staphylococcus aureus | .195 | .177 | 0.078 | 0.098 | 0.195 | 0.138 | 0.098 | 0.055 |
| Escherichia coli | 6.25 | 5.69 | 3.12 | 3.94 | 3.125 | 4.44 | 3.125 | 3.5 |
| Klebsiella pneumoniae | .78 | .71 | 0.39 | 0.98 | 0.39 | 1.108 | 0.195 | 0.437 |
| Salmonella schottmuelleri | .78 | 1.42 | 0.78 | 0.98 | — | — | — | — |
| Salmonella typhosa | .39 | .35 | 0.31 | 0.12 | — | — | — | — |
| Proteus vulgari | — | — | — | — | 0.78 | 0.554 | — | — |
| Streptococcus pneumonia II | — | — | — | — | — | — | 0.049 | 0.027 |

EXAMPLE 11

The compounds of this invention, as well as amoxicillin, were tested to determine their in vivo activity against representative systemic Gram positive and Gram negative bacterial infections in mice with both oral and subcutaneous administration. The PD$_{50}$ is the protective dose for 50% of the animals treated against a challenge organism.

Results are reported in Table 4 below.

TABLE 4

In vivo Activity

(a) Subcutaneous Administration PD$_{50}$

| Organism | Amoxicillin | I | Amoxicillin | II | Amoxicillin | III | Amoxicillin | IV |
|---|---|---|---|---|---|---|---|---|
| S. pyogenes | 1.2 | 7.0 | 2.5 | 3.4 | 3.5 | 4.1 | 2.3 | 4.4 |
| S. pneumoniae I | .35 | .7 | 0.6 | 0.7 | 3.0 | 2.5 | 0.9 | 0.9 |
| E. coli | 10 | 8.2 | 5.9 | 18 | 7.3 | 19.4 | 6.8 | 10.4 |
| K. pneumoniae | 3.6 | 3.8 | 5 | 5.7 | 5.0 | 5.3 | 3.7 | 2.4 |
| S. schottmuelleri | 1.5 | 2.4 | 4.7 | 5.7 | — | — | — | — |
| S. typhosa | 2.7 | 7.3 | 0.95 | 1.4 | — | — | — | — |
| S. aureus | — | — | <0.2 | 0.5 | — | — | <0.2 | 0.34 |
| S. pneumoniae II | — | — | — | — | 1.6 | 3.2 | 0.6 | 0.5 |
| P. mirabilis | — | — | — | — | <0.5 | 2.5 | 0.6 | 0.4 |
| P. aeruginosa | — | — | — | — | >200 | >142 | — | — |

(b) Oral Administration PD$_{50}$

| Organism | Amoxicillin | I | Amoxicillin | II | Amoxicillin | III | Amoxicillin | IV |
|---|---|---|---|---|---|---|---|---|
| S. pyogenes | 1.0 | 3.8 | 1.4 | 1.9 | 6.1 | 6.3 | 8.3 | 6.0 |
| S. pneumoniae I | .85 | 1.5 | 0.8 | 0.7 | 2.3 | 4.7 | 1.3 | 0.7 |
| E. coli | 14.1 | 23.8 | 18.5 | 23 | 19.3 | 18.7 | 13.1 | 22.1 |
| K. pneumoniae | 5.0 | 9.9 | 10.8 | 8.6 | 4.3 | 15.5 | 6.1 | 4.8 |
| S. schottmuelleri | 1.8 | 5.4 | 7.6 | 1.9 | — | — | — | — |
| S. typhosa | 13.3 | 8.0 | 3.7 | 3.6 | — | — | — | — |
| S. aureus | — | — | 0.5 | 0.6 | — | — | 0.6 | 1.2 |
| S. pneumoniae II | — | — | — | — | 1.6 | 3.2 | 0.7 | 0.7 |
| P. mirabilis | — | — | — | — | 1.8 | 3.8 | 1.1 | 1.6 |
| P. aeruginosa | — | — | — | — | >200 | >142 | — | — |

EXAMPLE 12

| Item | Ingredients | mg/tablet 100 mg | 250 mg | 500 mg |
|---|---|---|---|---|
| 1. | {2S-[2α,5α,6β(S*)]}-6-{[tetrahydro-2-thienyl-amino-(4-hydroxyphenyl)acetyl]amino}-3,3-dimethyl-7-oxo-4-thia-1-azabicyclo[3.2.0]heptane-2-carboxylic acid sodium salt | 100 | 250 | 500 |
| 2. | Lactose | 147.5 | 100 | 97.5 |
| 3. | Pregelatinized Starch | 25 | 30 | 60 |
| 4. | Modified Starch | 25 | 50 | 60 |
| 5. | Cornstarch | 25 | 50 | 60 |
| 6. | Magnesium Stearate | 2.5 | 5 | 7.5 |
| | Tablet weight | 325 mg | 500 mg | 785 mg |

Procedure:
(1) Mix Items 1–5 in a suitable mixer, granulate with water, and dry overnight in a suitable oven. Mill through suitable mill.
(2) Mix with Item 6 and compress on a suitable press.

EXAMPLE 13

A tablet was prepared in the same manner as in Example 12 except that {2S-[2α,5α,6β(S*)]}-6-(Bis(tetrahydro-2H-pyran-2-yl)amino]}[(hydroxyphenyl)acetyl]amino}-3,3-dimethyl-7-oxo-4-thia-1-azabicyclo[3.2.0]heptane-3-carboxylic acid sodium salt was the active ingredient.

EXAMPLE 14

A tablet was prepared in the same manner as in Example 12 except that 2S-[2α,5α,6β(S*)-6-{Bis[ethyl-3-fluoro-2-tetrahydrofuranylamino-(4-hydroxyphenyl)acetyl]amino}-3,3-dimethyl-7-oxo-4-thia-1-azabicyclo-[3.2.0]heptane-2-carboxylic acid sodium salt was the active ingredient.

EXAMPLE 15

| | | Capsule Formulation | | |
|---|---|---|---|---|
| Item | Ingredients | mg/capsule 100 mg | 250 mg | 500 mg |
| 1. | {2S-[2α,5α,6β(S*)]}-6-[Bis(tetrahydro-2H-pyran-2-yl)amino]{[(4-hydroxyphenyl)acetyl]amino}-3,3-dimethyl-7-oxo-4-thia-]-aza-bicyclo[3.2.0]heptane-3-carboxylic acid sodium salt | 100 | 250 | 500 |
| 2. | Lactose | 99 | 148 | — |
| 3. | Cornstarch | 20 | 30 | 57 |
| 4. | Talc | 5 | 10 | 15 |
| 5. | Magnesium Stearate | 1 | 2 | 3 |
| | Capsule fill weight | 225 mg | 440 mg | 575 mg |

Procedure:
(1) Mix Items 1–3 in a suitable mixer. Mill through a suitable mill.
(2) Mix the mixture in Step 1 with Items 4, 5, and fill on a suitable machine.

EXAMPLE 16

A capsule was prepared in the same manner as in Example 15 except that {2S-[2α,5α,6β(S*)]}-6-{[tetrahydro-2-thienylamino-(4-hydroxyphenyl)acetyl]amino}-3,3-dimethyl-7-oxo-4-thia-1-azabicyclo[3.2.0]heptane-2-carboxylic acid sodium salt was the active ingredient.

EXAMPLE 17

A capsule was prepared in the same manner as in Example 15 except that {2S-[2α,5α,6β(S*)]}-6-{Bis[ethyl-3-fluoro-2-tetrahydrofuranylamino-(4-hydrophyphenyl)acetyl]amino}-3,3-dimethyl-7-oxo-4-thia-1- azabicyclo-[3.2.0]heptane-2-carboxylic acid sodium salt was the active ingredient.

EXAMPLE 18

| Formulation | 100 mg/ container | 200 mg/ container | 500 mg/ container | 1 liter |
|---|---|---|---|---|
| {2S-[2α,5α,6β(S*)]}-6-[Bis(tetra-hydro-2H-pyran-2-yl)amino]{[(4-hydroxyphenyl)acetyl]amino}-3,3-dimethyl-7-oxo-4-thio-1-azabicyclo-[3.2.0]heptane-3-carboxylic acid sodium salt | 110 mg | 220 mg. | 550 mg. | 200.0 gm. |
| Water for Injection | 0.55 ml. | 1.10 ml. | 2.75 ml. | 1000 ml. |

Manufacturing Procedure

Dissolve 200 gm. of {2S-[2α,5α,6β(S*)]}-6-[Bis(tetrahydro-2H-pyran-2-yl)amino]-{[(4-hydroxyphenyl)acetyl]amino}-3,3-dimethyl-7-oxo-4-thia-1-azabicyclo[3.2.0]heptane-3-carboxylic acid sodium salt as a lyophilized powder with stirring in 800 ml. of Water for Injection. Enough Water was added to make 1000 ml. Pass the solution through a sterile Millipore filter apparatus fitted with a 0.22 micron porosity filter. Alternately the solution may be filtered through a sterile ceramic filter candle. Collect the filtrate into a sterile container.

Fill the following volumes of solution into suitable sterile containers to obtain the desired quantity of drug per container.

| Quantity of Drug per Container | Volume of Solution to be Filled into Container |
|---|---|
| 100 mg. | 0.55 ml. |
| 200 mg. | 1.10 ml. |
| 500 mg. | 2.75 ml. |

Transfer the filled containers to a suitable sterile lyophilizer. Sterile thermocouples are placed into appropriate containers throughout the lyophilizer to check the temperature of the contents throughout the lyophilization cycle. The solution in the containers is frozen to a temperature of −40° C. Vacuum is then applied and the temperature of the lyophilizer shelves are gradually raised to a temperature of 35° C. to 40° C. The vacuum is broken by admitting sterile nitrogen into the lyophilizer chamber. The containers are sealed with sterile rubber stoppers and a three-piece metal vial seal is crimped over the stopper and the container lip.

When reconstituting the lyophilized powder use sterile Water for Injection U.S.P. or Sodium Chloride Injection U.S.P.

| Container Size | Minimum Amount of Diluent to be Added |
|---|---|
| 100 mg. | 0.5 ml. |
| 200 mg. | 1.0 ml. |
| 500 mg. | 2.5 ml. |

EXAMPLE 19

A sterile injectable solution was prepared in accordance with Example 18 utilizing {2S-[2α,5α,6β(S*)]}-6-{[tetrahydro-2-thienylamino-(4-hydroxyphenyl)acetyl]amino}-3,3-dimethyl-7-oxo-4-thia-1-azabicyclo[3.2.0]heptane-2-carboxylic acid sodium salt as the active ingredient.

We claim:

1. A compound of the formula:

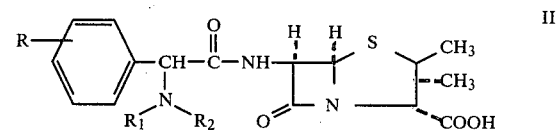

wherein R is hydrogen or hydroxy, $R_1$ and $R_2$ are individually hydrogen, or a saturated heterocyclic 5 to 6 membered ring containing one hetero atom selected from the group consisting of oxygen and sulfur, said hetero atom being positioned in said ring adjacent the carbon atom in said ring connected to the nitrogen atom, said ring being unsubstituted or substituted in one or more positions with lower alkyl or halogen, with the proviso that at least one of $R_1$ and $R_2$ is other than hydrogen;

salts, hydrates or esters thereof.

2. The compound of claim 1 wherein said penicillin is {2S-[2alpha,5alpha,6beta(S*)]}-6-{[2-tetrahydrofuranylamino(4-hydroxyphenyl)acetyl]amino}-3,3-dimethyl-7-oxo-4-thia-1-azabicyclo[3.2.0]heptane-2-carboxylic acid.

3. The compound of claim 1 wherein said penicillin is {2S-[2alpha,5alpha,6beta(S*)]}-6-[bis(tetrahydro-2H-pyran-2-yl)amino]{[(4-hydroxyphenyl)acetyl]amino}-3,3-dimethyl-7-oxo-4-thia-1-azabicyclo[3.2.0]heptane-3-carboxylic acid.

4. The compound of claim 1 wherein said penicillin is {2S-[2alpha,5alpha,6beta(S*)]}-6-{[tetrahydro-2-thienylamino-(4-hydroxyphenyl)acetyl amino}-3,3-dimethyl-7-oxo-4-thia-1-azabicyclo[3.2.0]heptane-2-carboxylic acid.

5. The compound of claim 1 wherein said penicillin is {2S[2alpha,5alpha,6beta(S*)]}-6-{Bis[5-ethyl-3-fluoro-2-tetrahydrofuranylamino-(4-hydroxyphenyl)-acetyl]amino}-3,3-dimethyl-7-oxo-4-thia-1-azabicyclo-[3.2.0]heptane-2-carboxylic acid.

* * * * *